(12) United States Patent
Deshpande et al.

(10) Patent No.: US 8,741,953 B2
(45) Date of Patent: Jun. 3, 2014

(54) TOPICAL FORMULATION FOR DIABETIC FOOT ULCERS

(75) Inventors: Supreet K Deshpande, Pune (IN); Sudhir A. Kulkarni, Pune (IN); Reena Gollapudy, Pune (IN)

(73) Assignee: Vlife Sciences Technologies Pvt. Ltd., Pune (IN)

( * ) Notice: Subject to any disclaimer, the term of this patent is extended or adjusted under 35 U.S.C. 154(b) by 0 days.

(21) Appl. No.: 13/497,362

(22) PCT Filed: Sep. 21, 2010

(86) PCT No.: PCT/IN2010/000637
§ 371 (c)(1),
(2), (4) Date: Mar. 21, 2012

(87) PCT Pub. No.: WO2011/039780
PCT Pub. Date: Apr. 7, 2011

(65) Prior Publication Data
US 2012/0196930 A1 Aug. 2, 2012

(30) Foreign Application Priority Data

Sep. 22, 2009 (IN) .......................... 1476/MUM/2009

(51) Int. Cl.
*A01N 37/12* (2006.01)
(52) U.S. Cl.
USPC ....................................................... 514/538
(58) Field of Classification Search
USPC ....................................................... 514/538
See application file for complete search history.

(56) References Cited

U.S. PATENT DOCUMENTS

| | | | |
|---|---|---|---|
| 4,857,552 A | | 8/1989 | Rosenberg et al. |
| 5,017,609 A | | 5/1991 | Escobar et al. |
| 5,284,833 A | * | 2/1994 | McAnalley et al. ............ 514/23 |
| 6,310,094 B1 | | 10/2001 | Liu et al. |
| 6,528,540 B2 | | 3/2003 | Liu et al. |
| 7,083,806 B2 | * | 8/2006 | Rippon et al. ................ 424/484 |

FOREIGN PATENT DOCUMENTS

| | | | |
|---|---|---|---|
| WO | 02/076446 | | 10/2002 |
| WO | WO-02/076446 A1 | * | 10/2002 |
| WO | 2008/093356 | | 8/2008 |
| WO | WO-2008/093356 A1 | * | 8/2008 |
| WO | 2008/147715 | | 12/2008 |
| WO | 2009/073658 | | 6/2009 |

OTHER PUBLICATIONS

International Search Report for international application No. PCT/IN2010/000637, dated Jul. 10, 2011 (3 pages).
Snyder, "Treatment of nonhealing ulcers with allografts," Clinics in Dermatology, 2005, vol. 23, pp. 388-395.
Salcido et al., "Animal models in pressure ulcer research," J Spinal Cord Med., 2007, vol. 30, pp. 107-116.
Rosenberg et al.,"An accurate prediction of the pH change due to degradation: correction for a "produced" secondary buffering system," Parmaceutical Research, 1988, vol. 5, No. 8, pp. 514-517.
Mustoe, "Understanding chronic wounds: a unifying hypothesis on their pathogenesis and implications for therapy," The American Journal of Surgery, 2004, vol. 187, pp. 65S-70S.
American Burn Association, "Burn Incidence and Treatment in the United States: 2011 Fact Sheet", accessed Mar. 21, 2012 <http://www.ameriburn.org/resources_factsheet.php>.
Kuhn et al., "Balancing the pressure ulcer cost and quality equation," Nursing Economics, 1992, vol. 10, No. 5, pp. 353-359.
Tanahashi et al., "Comparative effects of ultra-short-acting β1-blockers on voltage-gated tetrodotoxin-resistance Na+ channels in rat sensory neurons," European Journal of Anaesthesiology, 2009, vol. 26. No. 3, pp. 196-200.
Brem et al., "Protocol for successful treatment of venous ulcers," The American Journal of Surgery, 2004, vol. 188, pp. 1S-8S.
Kosiak, "Etiology and pathology of ischemic ulcers," Archives of Physical Medicine & Rehabilitation, 1959, vol. 40, pp. 62-69.

* cited by examiner

*Primary Examiner* — Ali Soroush
(74) *Attorney, Agent, or Firm* — Hamre, Schumann, Mueller & Larson, P.C.

(57) ABSTRACT

This invention relates to a new topical gel formulation of the drug Esmolol hydrochloride for treatment of chronic wounds such as diabetic wounds, burn wounds, venous ulcers and pressure ulcers.

6 Claims, No Drawings

TOPICAL FORMULATION FOR DIABETIC FOOT ULCERS

FIELD OF INVENTION

This invention relates to a new topical gel formulation of the drug Esmolol hydrochloride for treatment of chronic wounds such as diabetic wounds, burn wounds, venous ulcers and pressure ulcers.

BACKGROUND OF INVENTION

Chronic wounds are non healing wounds that do not follow pathophysiology of ordinary wounds. Chronic wounds are normally stuck in one of the phases of wound healing, usually in the inflammatory phase. The chronic wounds cause significant physical emotional and financial burden on the patients. Chronic wounds may include chronic ulcers, such as venous ulcers, diabetic ulcers, pressure ulcers and burn ulcers.

Diabetic foot problems are among the most serious and costly complications of diabetes. The rising prevalence of diabetes all over the world has brought with it an increase in the number of lower limb amputations performed as a result of the disease. Epidemiological reports indicate that over one million amputations are performed on people with diabetes each year. This amounts to a leg being lost to diabetes somewhere in the world every 30 seconds.

A majority of these amputations are preceded by diabetic foot ulcers (DFU). Only two-thirds of ulcers will eventually heal and the remainder may result in some form of amputation. The median time of healing for an ulcer is approximately six months. Both ulcers and amputations have an enormous impact on people's lives, often leading to reduced independence, social isolation and psychological stress. The diabetic foot is also a significant economic problem, particularly if amputation results in prolonged hospitalization, rehabilitation, and an increased need for home care and social services. In absence of effective, affordable therapies, the current standard of care for the DFU is dressing, keeping the wound clean and off-loading the wound. The only approved treatment available for DFU is in the form of topical gel of platelet derived growth factor, Regranex®. Thus, the treatment options for DFU are limited.

Venous ulcers (or varicose ulcers) are wounds that are thought to occur due to improper functioning of valves in the veins usually of the legs. They are the major cause of chronic wounds, occurring in 70% to 90% of chronic wound cases (Snyder R. J., Clin. Dermatol. 2005, 23: 388-95). It is estimated that venous stasis ulcers affect 500-600,000 people in the United States every year and it is by far the most common type of leg ulcer seen. This type of ulcer accounts for the loss of 2 million working days and incurs treatment costs closing in on $3 billion dollars per year in the USA. Although compression therapy has been the gold standard of treatment of venous stasis ulcers, there are some individuals that cannot tolerate compression over the ulcer; as the pain is just too great. In recent years a drug call pentoxifylline (Trental) has been used with a reasonable amount of success.

Pressure ulcers (PUs), also known as decubitus ulcers, bed sores or pressure sores, are pathomechanically and pathophysiologically induced ischemic-reperfusion injuries that primarily result from unrelieved pressure (Salcido et al., J Spinal Cord Med. 2007; 30:107-116). An estimated 1.3 to 3 million patients in the US have pressure ulcers (PUs); incidence is highest in older patients, especially those who are hospitalized or in long-term care facilities. Aging increases risk, in part because of reduced subcutaneous fat and decreased capillary blood flow. Immobility and comorbidities increase risk further. Annual costs directly related to PU treatment have been estimated to be $3.5 to $7.0 billion a year (Kuhn B A and Coulter S J., Nurs Econ. 1992, 10:353-9). The prevalence of PUs is estimated at 3% to 10% of all hospitalized patients and from 20% to 32% of all elderly hospitalized patients with long-term disabilities (Kosiak M., Arch Phys Med. Rehabil. 1959; 40(2):62-69).

Burn wounds can be caused by various factors like heat, light, electricity, chemicals, etc. The burns depths are described as either superficial, superficial partial-thickness, deep partial-thickness, or full-thickness. About 0.5 million cases are reported every year of burn injuries in US as per the fact sheet "Burn Incidence and Treatment in the United States: 2012 Fact Sheet" (American Burn Association National Burn Repository (2012 report)). Burn injuries are responsible for about 3,000-5,000 deaths per year in the US. The worldwide incidence of fire-related injuries in 2004 was estimated to be 1.1 per 100,000 population, with the highest rate in Southeast Asia and the lowest in the Americas.

A topical treatment for wounds or ulcers is easier to apply and has fewer side effects compared to other routes of administration. In addition, topical drugs having shorter half life have better safety profile than others.

Esmolol hydrochloride is a short-acting beta-1 adrenergic receptor blocker used for treatment or prophylaxis of cardiac disorders in mammals. Esmolol hydrochloride possesses the selective beta-1-adrenergic blocking activity; however, at high concentration it also blocks beta-2-adrenergic receptor. In contrast to conventional beta-blocking compounds, Esmolol hydrochloride contains an ester group leading to its unique short half life of nine minutes.

The presence of ester group in Esmolol makes it prone to degradation due to hydrolysis. This property of Esmolol poses significant challenge in generating its stable formulation. Esmolol hydrochloride is found to be stable around pH of between about 4 and 6, and this is normally achieved by addition of buffers to Esmolol solution. Various formulations of Esmolol hydrochloride have been reported for parenteral administration (U.S. Pat. No. 4,857,552, WO02/076446, U.S. Pat. No. 5,017,609, U.S. Pat. No. 6,528,450, U.S. Pat. No. 6,310,094, WO2008/147715). A topical formulation of Esmolol hydrochloride has not been reported. The present invention provides a topical, dermal formulation that is a tissue adherent thermo-reversible polymeric gel suitable for application on chronic wounds.

SUMMARY OF INVENTION

The present invention relates to a new topical gel formulation, as well as a method of producing this pharmaceutical composition suitable for treatment of chronic wounds, more specifically, diabetic foot ulcers. The topical formulation may comprise the active pharmaceutical ingredient (API) methyl-3-[4-(2-hydroxy-3-isopropylamino) propoxy]phenyl propionate hydrochloride (Esmolol hydrochloride), poloxamer 338, purified water, buffers such as acetate buffer, hydrochloric acid for pH adjustment and an antimicrobial 50% Benzalkonium Chloride.

DETAILED DESCRIPTION OF INVENTION

In accordance with this detailed description, the following abbreviations and definitions apply. It must be noted that as used herein, the singular forms "a", "and", and "the" include plural referents unless the context clearly dictates otherwise.

Thus, for example, reference to "the dosage" includes reference to one or more dosages and equivalents thereof known to those skilled in the art.

By the term "subject" or "patient" as used herein is meant to include a mammal. The mammal can be a canine, feline, primate, bovine, ovine, porcine, camelid, caprine, rodent, or equine. Preferably the mammal is human.

By the phrases "pharmaceutically acceptable carrier" and "pharmaceutically acceptable excipient" are intended to mean any compound(s) used in forming a part of the formulation that is intended to act merely as a carrier. The pharmaceutically acceptable carrier or excipient is generally safe, non-toxic, and neither biologically nor otherwise undesirable. A pharmaceutically acceptable carrier or excipient as used herein includes both one and more than one such carrier or excipient.

The present invention is generally in the field of controlled drug delivery and particularly in the area of direct delivery of a new topical formulation of Esmolol hydrochloride to the surface of chronic wounds. The present invention provides a pharmaceutical composition for treatment of chronic wounds including diabetic foot ulcers, venous ulcers, pressure ulcers and burn ulcers.

The chronic wounds are caused by several causes such as vascular insufficiency and diabetes. Amongst the host of complications caused by chronic diabetes, diabetic foot ulcer (DFU) is one of the most critical and life threatening fall-outs, due to its likely progression into a sepsis like condition leading to amputation and ultimately death. Diabetes is the leading cause of non-traumatic lower extremity amputations worldwide and foot ulcers are a major predictor of future amputation in subjects with diabetes. Even without amputation, DFU contribute a major economic burden to society and impair quality of life for the individual. The standard of care for treatment of diabetic foot ulcer requires moist wound environment. This is usually provided through use of moist dressings. A suitable topical dermal composition for treatment of DFU requires easy application and adherence to wound surface.

The exact etiology of venous ulcers is not certain, but they are thought to arise when venous valves that exist to prevent backflow of blood do not function properly, causing the pressure in veins to increase (Brem et. al., Am. J. Surg. 2004, 188 (1A Suppl): 1-8; Mustoe T., Am. J. Surg. 2004, 187 (5A): 658-70S). The body needs the pressure gradient between arteries and veins in order for the heart to pump blood forward through arteries and into veins. When venous hypertension exists, arteries no longer have significantly higher pressure than veins, blood is not pumped as effectively into or out of the area and it pools. Venous hypertension may also stretch veins and allow blood proteins to leak into the extravascular space, isolating extracellular matrix (ECM) molecules and growth factors, preventing them from helping to heal the wound. Pressure Ulcers are accepted to be caused by three different tissue forces:

i. Pressure, or the compression of tissues
  ii. Shear force, or a force created when the skin of a patient stays in one place as the deep fascia and skeletal muscle slide down with gravity
  iii. Friction or a force resisting the shearing of skin.

Pressure ulcers are areas of necrosis and ulceration where tissues are compressed between bony prominences and hard surfaces. Risk factors include old age, impaired circulation, immobilization, malnourishment, and incontinence. These injuries range in clinical severity from stage I to stage IV. Stage I PUs are considered the least severe clinically and consist of intact skin that appears pink or red in ambient light and does not turn white (nonblanching erythema) when manual pressure is applied. Stage IV PUs includes major damage that extends through the skin and muscle down to the bone. Although this classification is used in clinical practice, it does not necessarily relate to the origin of the lesion or the temporal progression or healing of the ulcer (does not represent an ordinal scale). Severity ranges from nonblanchable skin erythema to full-thickness skin loss with extensive soft-tissue necrosis. Treatment includes pressure reduction, avoidance of friction and shearing forces, local care, and sometimes skin grafts or myocutaneous flaps.

The pharmaceutical composition of this invention is a hydro gel thereby provides a moist environment to the wound. The formulation is contained in the tube in a liquefied form and forms a uniform gel upon exposure to the broken, fractured wound site. Thus, the formulation adheres to the wound site to provide the active pharmaceutical ingredient (API). The gel is liquid at 4° C. and solid at body temperature and is fluid at 25° C. The pharmaceutical composition of this invention is thus a topical gel formulation that fulfills provides a moist environment as well as wound adherence.

The present formulation provides a stable, clear transparent, colourless gel. It is known that Esmolol is unstable due to presence of an ester group. Hydrolysis of this ester group causes degradation of the drug (Rosenberg et al., 1988, Pharma. Res., 5, 514-517). Hence, the stable pH range is between 4 and 6, with pH around 5 being the optimum pH for highest stability. Accordingly, a pH of 5 was found to be optimal for a formulation.

Preformulation studies including physicochemical analysis of Esmolol Hydrochloride and solubility study as outlined above were performed. Acidity/Alkalinity of an aqueous solution of the API at various concentrations was also determined.

Since Esmolol hydrochloride has a short pharmacological half life of about 9 minutes when administered, it has only been utilized for acute conditions. For it to be useful for chronic conditions like the treatment of chronic wounds, a topical formulation with high concentrations of Esmolol hydrochloride would be required.

The pre-clinical studies for wound healing in diabetic rats suggest that the effective concentration was in the range of 10% to 20% (WO 2008/093356). Therefore in the development of the present formulation, it was critical to choose appropriate gelling agent that can form stable gel with high concentration of Esmolol hydrochloride.

Several gelling agents known in pharmaceutical compositions were tried to formulate stable gel with high concentration (20% w/w) of Esmolol hydrochloride. However, most gelling agents could not form stable gel at such high concentration of active ingredient. For example, gelling agents of various grades and concentrations explored for formulation were hydroxypropylmethyl cellulose, sodium carboxymethylcellulose, potato starch and carrageenan. The gels either were not properly formed or were unstable even at room temperature. However, surprisingly, poloxamer 338 was found to be suitable gelling agent that forms stable gel at high concentrations of Esmolol hydrochloride.

Poloxamer 338 is water soluble and forms hydrogel at appropriate concentrations that can hold water in the formulation and provide moist environment to the wound. A further advantage of poloxamer 338 is due to its surfactant property or detergent action which cleanses the wound and enables debridement of non viable tissues.

In order to stabilize the pH of the formulation, various buffer systems such as citrate buffer and acetate buffer were then tried. The quantity of citric acid required for pH adjustment was beyond that permitted as per the IIG database, and thus the acetate buffer was preferred. Initial trials with acetate buffer containing 0.03% of sodium acetate trihydrate showed lowering of pH values within 7 days of storage at 40° C./75% RH which indicated that buffer activity was inadequate. In further trials the concentration was increased to 0.3% and pH was adjusted to 5.0 using glacial acetic acid. In the subsequent trial, glacial acetic acid concentration was reduced to 0.0546% and pH was adjusted to 5.0 by addition of concentrated Hydrochloric acid (0.0238%).

In order to select a suitable preservative system for the formulation, a combination of methyl and propyl parabens was tried, but this resulted in a colour change in the product under stress conditions. A further attempt was also made to include Benzyl alcohol at a concentration of 2.7% as preservative but the drop of pH was seen when the composition was subjected to accelerated stability conditions. The use of benzalkonium solution did not show such adverse effects on the formulation, hence its use was finalized.

Drug-excipient compatibility studies were carried out and promising batches were subjected to stress testing in the form of short term stability studies in various packs for up to three months. Forced degradation studies and preservative efficacy testing were also carried out, and results were found to be satisfactory.

Using the optimized buffer and preservative systems, batches for 14% and 20% strength were also taken and were found to have acceptable physicochemical properties.

Composition of Gel Formulation

The composition contains methyl-3-[4-(2-hydroxy-3-isopropylamino) propoxy]phenyl propionate hydrochloride (Esmolol hydrochloride) as the API in an effective amount to heal diabetic foot ulcers. The composition also contains a biocompatible, polymeric matrix that is tissue adherent and biodegradable and has thermo-reversible properties. In addition, benzalkonium chloride is used as an antimicrobial additive and a buffer to reduce degradation of the esmolol hydrocloride.

The polymeric matrix present in the topical formulation consists of Pluracare® F108NF which is poloxamer 338. Poloxamers are block copolymers, commercially available for example from BASF corporation under trade names Pluronic® and Lutrol®. These are synthetic copolymers of ethylene oxide and propylene oxide. The poloxamers function as surfactants, emulsifiers, solubilizers and stabilizers in preparations. The physical forms of the poloxamer include a form of prills, cast solid and pastilles. It has a mild odor of polyol and is white to cream in color. The molecular formula for poloxamer 338 is $HO(C_2H_4O)_a(C_3H_6O)_b(C_2H_4O)_aH$ with a=141 and b=44. The poloxamer 338 is soluble in water and at concentration greater than 25% it forms a gel. The poloxamer has the unique property of forming thermo-reversible gels at or above 20° C. These gels are liquid at 2-8° C. temperature and solidify at room temperature (25-30° C.).

50% benzalkonium chloride is a biocide used in pharmaceutical antimicrobial preparations. Quaternary ammonium compounds belong to a group of ammonium salts in which organic radicals have been substituted for all four hydrogens of the original ammonium cation. They have a central nitrogen atom which is joined to four organic radicals and one acid radical. The organic radicals may be alkyl, aryl, or aralkyl, and the nitrogen can be part of a ring system. They are prepared by treatment of an amine with an alkylating agent. They show a variety of physical, chemical, and biological properties and most compounds are soluble in water and strong electrolytes. Such compounds include benzalkonium chloride and benzalthonium chloride among others. They have properties of disrupting micro-organisms' cell processes and surfactants. The addition of benzalkonium chloride to the composition hinders growth of microbes.

Acetate and citrate buffers may be used to stabilize the degradation of Esmolol hydrochlorid. The acetate buffer may include sodium acetate trihydrate and glacial acetic acid. The citrate buffer may include sodium citrate dihydrate and citric acid.

Esmolol hydrochloride exhibits stability and reduces degradation at pH between 4 and 6. Therefore, the pH of composition of topical gel formulation is required to be about pH 5.0, which is achieved by addition of hydrochloric acid to the formulation.

The active pharmaceutical agent in the present invention is Esmolol hydrochloride. The present formulation provides Esmolol hydrochloride in the range of about 0.001% to about 50% as the active pharmaceutical ingredient. More preferred concentrations of Esmolol hydrochloride are in the range of about 1% to about 20%. The most preferred concentrations of Esmolol hydrochloride of diabetic wound healing are in the range of about 10% to about 20%.

The excipient poloxamer 338 used in the present composition is present in the range of about 1% to about 40%. The preferred concentration of poloxamer 338 is in the range of about 25% to about 40% to achieve thermo reversible gel. The most preferred concentration of poloxamer 338 is in the range of about 27% to about 30%.

The 50% benzalkonium chloride used in the present composition is in the range of about 0.001% to about 1.0%. The preferred concentration of 50% benzalkonium chloride used in the present composition is in the range of about 0.1% to about 0.3%. The most preferred concentration of 50% benzalkonium chloride used in the present composition is in the range of about 0.25% to about 0.3%.

Acetate and citrate buffers may be used in the composition to stabilize the degradation of Esmolol hydrochloride. The acetate buffer is preferred over citrate buffer, because the quantity of citric acid required to stabilize pH at 5.0 was above permitted limits. The acetate buffer used in the present composition has sodium acetate trihydrate in the range of about 0.1% to about 0.4%, whereas glacial acetic acid in the range of about 0.01% to about 0.1%. The preferred concentration of sodium acetate trihydrate is in the range of about 0.2% to about 0.3%, whereas glacial acetic acid in the range of about 0.03% to about 0.07% in the acetate buffer. The most preferred concentration of sodium acetate trihydrate is in the range of about 0.27% to about 0.29%, whereas glacial acetic acid in the range of about 0.05% to about 0.06% in the acetate buffer.

Because poloxamer 338 added in the composition has a basic pH around 6.5, hydrochloric acid is added to adjust the pH to of the formulation to between 4 and 6. The hydrochloric acid added in the composition may be the range of about 0.01% to about 0.1%. The preferred concentration of hydrochloric acid added in the composition is in the range of about 0.02% to about 0.08%. The most preferred concentration of hydrochloric acid added in the composition is in the range of about 0.02% to about 0.06%.

The topical dermal gel formulation described above is delivered topically at the wound or ulcer site in a gel composition through a tube such as aluminum, HDPE or lami tubes. The stability data obtained in different containers suggest that most preferred container is lacquered collapsible aluminum tube.

The formulation in the range of 10% to 20% of Esmolol hydrochloride is to be applied once or twice daily on the wound surface enough to completely cover the wound area.

The amount of formulation to be applied on the ulcer or wound depends on size of the wound; however application of 0.04-0.1 ml of formulation per $cm^2$ of wound was found to be effective dose for healing. The formulation gel can also provide moist environment to all chronic wounds and for exudating wounds, it can absorb the exudates and provide clean environment. The anti-nociceptive action of Esmolol (Tanahashi et al., Eur J Anaesthesiol. 2009 26:196-200) provides additional advantage of application of formulation on the burn wounds.

Example 1

The present example provides a new topical gel formulation of API for the treatment of diabetic wounds, more specifically diabetic foot ulcers. The composition comprises of the API, methyl-3-[4-(2-hydroxy-3-isopropylamino)propoxy]phenylpropionate hydrochloride (Esmolol hydrochloride), an excipient Pluracare® F108NF (Pluronic F108NF Prill Poloxamer 338 from BASF), purified water, acetate buffer, Hydrochloric acid and 50% Benzalkonium Chloride. The details for 14% and 20% formulations are given in tables 1 and 2.

TABLE 1

Composition of the 14% API gel

| Ingredients | Quantity (mg/g) | Percent | Function |
|---|---|---|---|
| Esmolol hydrochloride | 140.0 | 14.0 | Main active ingredient |
| 50% Benzalkonium chloride | 2.60 | 0.26 | Anti-microbial and preservative |
| Pluronic F108NF Poloxamer 338 (Pluracare® F108NF) | 300.0 | 30.0 | Thermo-reversible gelling agent |
| Glacial acetic acid | 0.546 | 0.0546 | Buffer component |
| Sodium acetate trihydrate | 2.80 | 0.280 | Buffer component |
| Concentrated Hydrochloric acid | 0.552 | 0.0552 | pH adjusting agent |
| Water | 553.502 | 55.3502 | Vehicle |

TABLE 2

Composition of the 20% API gel

| Ingredients | Quantity (mg/g) | Percent | Function |
|---|---|---|---|
| Esmolol hydrochloride | 200.0 | 20.0 | Main active ingredient |
| 50% Benzalkonium chloride | 2.60 | 0.26 | Anti-microbial and preservative |
| Pluronic F108NF Poloxamer 338 (Pluracare® F108NF) | 300.0 | 30.0 | Thermo-reversible gelling agent |
| Glacial acetic acid | 0.546 | 0.0546 | Buffer component |
| Sodium acetate trihydrate | 2.80 | 0.280 | Buffer component |
| Concentrated Hydrochloric acid | 0.238 | 0.0238 | pH adjusting agent |
| Water | 493.816 | 49.3816 | Vehicle |

Example 2

Procedure for Preparation of Gel

First, the purified water was placed in a mixing vessel. About 5% of the total quantity of water was set aside for rinsing. Benzalkonium chloride solution (50%) was added to the mixing vessel under stirring. The container of Benzalkonium chloride was rinsed with purified water and added to the mixing vessel The sodium acetate trihydrate was added to the mixing vessel under stirring, and it was stirred well until it completely dissolved. Glacial acetic acid was added to the mixing vessel under stirring. The container was rinsed with purified water and added to the mixing vessel. Concentrated hydrochloric acid was added to the mixing vessel under stirring. The container was rinsed with the remaining purified water and added to the mixing vessel. The solution was allowed to cool to about 8-10° C. and poloxamer 338 was then added under stirring. Stirring was continued until a uniform solution was formed. Esmolol hydrochloride was added to the mixing vessel under stirring, and stirring was continued until it completely dissolves and a uniform, homogenous solution was formed. The gel was stored at about 5°-10° C. for complete deaeration, and until the formulation formed a clear colorless gel free of lumps. The gel was allowed to attain room temperature. The gel manufactured as above was filled into 30 g lacquered, aluminum collapsible tubes.

Example 3

The 14% and 20% Esmolol hydrochloride topical gels manufactured as per Example 1 and Example 2 were subjected to a stability test. Tables 3 and 4 show conditions used for the stability test, pH change of composition and assay of Esmolol hydrochloride at definite time intervals.

TABLE 3

Stability of 14% Esmolol hydrochloride topical gel

| Condition | Test | Initial | 1 month | 2 month | 3 month | 6 month |
|---|---|---|---|---|---|---|
| 25° C. ± 2° C. and 60% RH ± 5% RH | pH as is (25° C. ± 2° C.) | 5.11 | 4.93 | 5.00 | 5.03 | 4.80 |
| | Esmolol HCl Assay | 99.33% | 99.96% | 99.58% | 99.44% | 97.22% |
| 40° C. ± 2° C. and 75% RH ± 5% RH | pH as is (25° C. ± 2° C.) | 5.11 | 4.82 | 4.85 | 4.81 | 4.50 |
| | Esmolol HCl Assay | 99.33% | 100.0% | 99.04% | 98.13% | 91.56% |

TABLE 4

Stability of 20% Esmolol hydrochloride topical gel

| Condition | Test | Initial | 1 month | 2 month | 3 month | 6 month |
|---|---|---|---|---|---|---|
| 25° C. ± 2° C. and 60% RH ± 5% RH | pH as is (25° C. ± 2° C.) | 5.17 | 5.10 | 5.04 | 5.02 | 4.79 |
| | Esmolol HCl Assay | 100.39% | 99.96% | 99.47% | 99.61% | 97.34% |
| 40° C. ± 2° C. and 75% RH ± 5% RH | pH as is (25° C. ± 2° C.) | 5.17 | 4.93 | 4.85 | 4.78 | 4.56 |
| | Esmolol HCl Assay | 100.39% | 99.91% | 98.40% | 98.26% | 92.17% |

Although the present invention has been described in detail with reference to examples above, it is understood that various modifications can be made without departing from the spirit of the invention, and would be readily known to the skilled artisan.

What is claimed is:

1. A topical gel formulation for the treatment of chronic wounds comprising:
   a. Esmolol hydrochloride at about 10% to about 20%;
   b. Poloxamer 338 at about 25% to about 35%;
   c. 50% benzalkonium chloride at about 0.2% to about 0.3%;
   d. sodium acetate trihydrate at about 0.2% to about 0.3%;
   e. glacial acetic acid at about 0.03% to about 0.07%;
   f. concentrated hydrochloric acid at about 0.02% to about 0.08%;
   g. purified water at about 40% to about 60%; and
   wherein the formulation has pH between 4.0 to 6.0 and having thermoreversible property and packaged in a suitable container.

2. The formulation of claim 1, comprising:
   a. 14% of Esmolol hydrochloride:
   b. 0.26% of 50% benzalkonium chloride;
   c. 30.0% of Poloxamer 338
   d. 0.0546% of glacial acetic acid;
   e. 0.28% of sodium acetate trihydrate;
   f. 0.0552% of hydrochloric acid; and
   g. 55.3502% of water.

3. The formulation of claim 1, comprising:
   a. 20% of Esmolol hydrochloride;
   b. 0.26% of 50% benzalkonium chloride;
   c. 30.0% of Poloxamer 338;
   d. 0.0546% of glacial acetic acid;
   e. 0.28% of sodium acetate trihydrate;
   f. 0.0238% of hydrochloric acid; and
   g. 49.3816% of water.

4. A method of preparation of a thermoreversible topical gel formulation as claimed in claim 1 for the treatment of chronic wounds comprising; the steps of:
   i) adding benzalkonium chloride solution (50%) to the required quantity of water in mixing vessel under stirring to form part I;
   ii) adding sodium acetate trihydrate to part I in the mixing vessel under stirring till it completely dissolve to form part II,
   iii) adding glacial acetic acid to part II in the mixing vessel under stirring to form part III;
   iv) adding hydrochloric acid to part III in the mixing vessel under stirring to form part IV;
   v) allowing the solution of part IV to cool to about 8-10° C. and adding Poloxamer 338 under stirring and continue stirring to form a uniform solution to form part V;
   vi) adding Esmolol hydrochloride to part V in the mixing vessel under stirring and continue stirring till it completely dissolves and a uniform, homogenous solution is formed.

5. The formulation of claim 1, wherein the chronic wounds are selected from the group consisting of diabetic foot ulcers, venous ulcers, pressure ulcers and burn wounds.

6. The formulation of claim 1, wherein the suitable container is a tube, bottle or spray device.

* * * * *